United States Patent [19]

Barnes et al.

[11] Patent Number: 4,542,744
[45] Date of Patent: Sep. 24, 1985

[54] METHOD AND APPARATUS FOR REMOTE TISSUE IDENTIFICATION BY STATISTICAL MODELING AND HYPOTHESIS TESTING OF ECHO ULTRASOUND SIGNALS

[75] Inventors: Casper W. Barnes, Newport Beach; Farhad Towfiq, Dana Pt., both of Calif.

[73] Assignee: North American Philips Corporation, New York, N.Y.

[21] Appl. No.: 478,172

[22] Filed: Mar. 23, 1983

[51] Int. Cl.⁴ ............................................. A61B 10/00
[52] U.S. Cl. ........................................ 128/660; 73/602
[58] Field of Search .................. 128/660, 663; 73/599, 73/602, 625–626

[56] References Cited

U.S. PATENT DOCUMENTS 4,414,850 11/1983 Miwa et al. ............................ 73/599
4,428,235 1/1984 Sugiyama ........................... 73/602 X

OTHER PUBLICATIONS

Chivers, R. C. et al., "Frequency Dependence of UTS Backscattering Cross-Sections: An Indicator of Tissue Structure Char.", Conf. 2nd Wd. Congress on UTS in Med., Rotterdam, Jun. 1973, pp. 300–303.
Lorenz, W. J. et al., "Computer Analysis of A–Scan for Detection of Generalized Diseases of the Liver", Proc. of 2nd European Cong. on UTS in Med., Munich, Germany, Mar. 1975.
Sokoller, A. et al., "Methods of Tissue ID by UTS Spectra", NBS Special Publ. 453, May 1975.

*Primary Examiner*—Kyle L. Howell
*Assistant Examiner*—Francis J. Jaworski
*Attorney, Agent, or Firm*—Jack E. Haken

[57] ABSTRACT

Apparatus and methods for remote identification of tissue types model the scattering of ultrasound energy from living tissue as an autoregressive or autoregressive moving average random process. Autoregressive or autoregressive moving average models of candidate tissue types are generated from pulse-echo data that is known to come from that particular tissue type. Kalman prediction error filters are used for each candidate tissue type to generate estimates of the probability that an unknown pulse echo signal belongs to the class generated by that tissue type. Unknown pulse-echo signals are filtered in a specific Kalman filter to test the hypothesis that the unknown signal belongs to the class associated with that particular Kalman filter.

60 Claims, 9 Drawing Figures

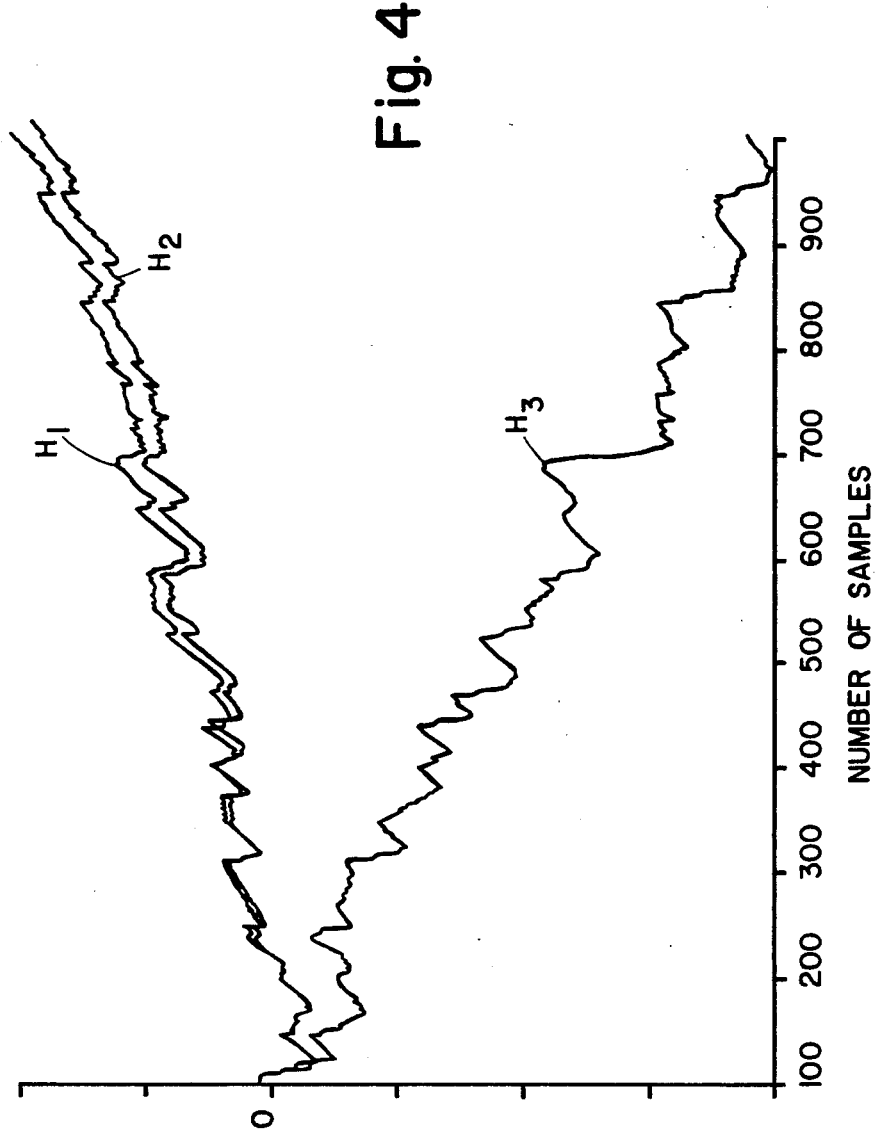

RELATIVE LOG LIKELIHOOD FUNCTIONS FOR SAMPLE 2

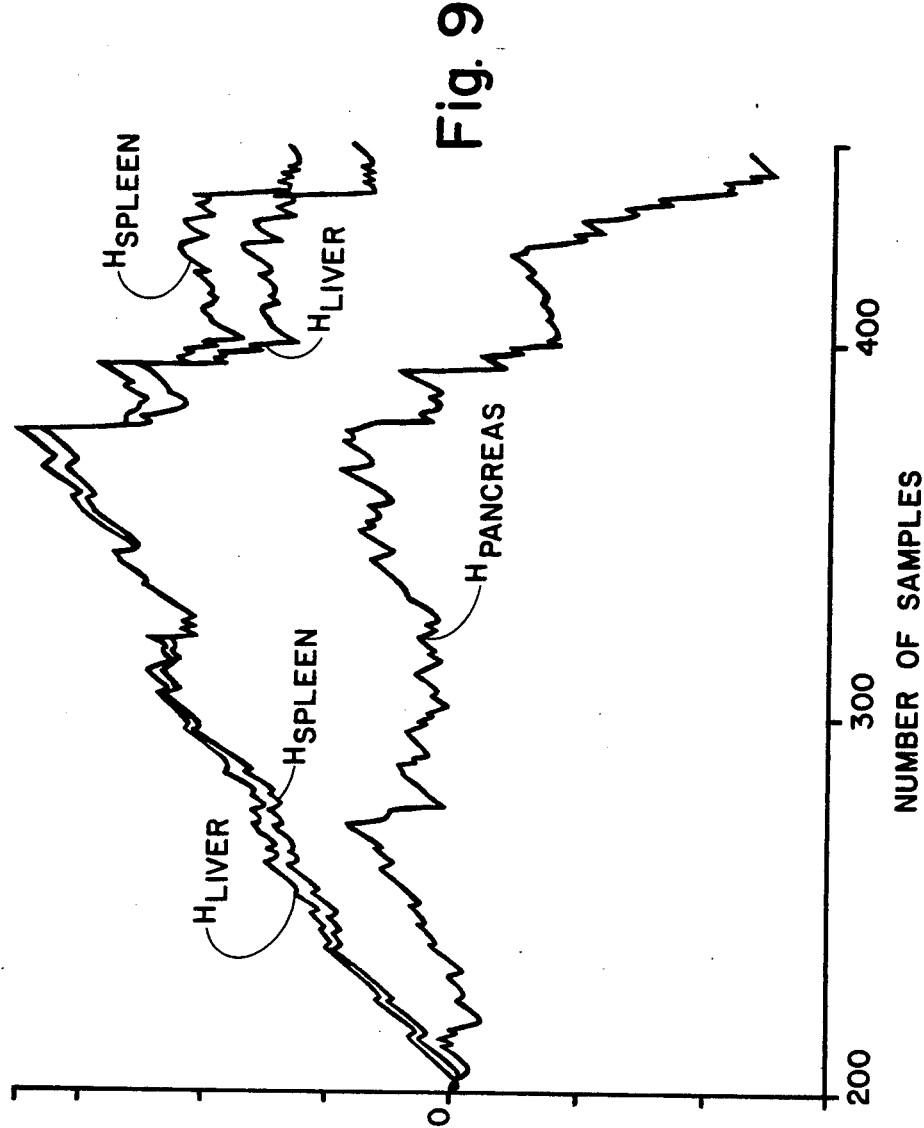

METHOD AND APPARATUS FOR REMOTE TISSUE IDENTIFICATION BY STATISTICAL MODELING AND HYPOTHESIS TESTING OF ECHO ULTRASOUND SIGNALS

FIELD OF THE INVENTION

The invention relates to methods and apparatus for characterizing tissue using ultrasound energy. The invention is particularly useful in connection with apparatus and methods for the diagnostic imaging of human and animal body structures.

BACKGROUND OF THE INVENTION

Methods and apparatus which utilize ultrasound energy for the diagnostic imaging of body structures are well known. Typically, ultrasound energy is directed into and scattered from body tissues. The amplitude of the resultant echoes is detected and displayed to form an image which characterizes the scattering structures. Virtually all commercial medical ultrasound imaging systems form images from the envelope of echoes which are reflected from an interface of tissue types such have different acoustic impedances. The images are, therefore, useful to delineate the outlines of various body organs and lesions. However, because the image makes no use of the phase information in the echo signals, it is not generally possible to identify tissues types.

The prior art teaches a number of ultrasound systems which are capable of identifying tissues having specific characteristics. U.S. Pat. No. 4,389,893 to by OPHIR and MAKLAD is typical of a class of apparatus which attempts to characterize tissue types by measuring local ultrasonic attenuation. Likewise, U.S. Pat. No. 4,270,546 to PERILHOU and COURSANT describes apparatus for identifying the directional characteristics of tissue structures.

The ultimate aim of tissue characterization apparatus and methods is, of course, to differentiate and identify the tissues of the various body organs as well as the pathology of healthy and diseased tissues to provide a remote, noninvasive biopsy. Although the methods and apparatus of the prior art may have some use in differentiating particular tissue characteristics, they have not yet attained these goals.

SUMMARY OF THE INVENTION

We have determined that ultrasonic pulse-echo data from different tissue types of pathologies exhibit differentiable statistical regularities. Tissue types of pathologies are classified by utilizing known modeling and hypothesis testing statistical techniques with a dedicated or general purpose digital computer.

Samples of a pulse-echo record from unknown tissue are treated as a vector $x = [x_1, x_2, \ldots, x_n]$. We hypothesize that this record was generated by one of a finite set of tissue types. $H_R$ denotes the hypothesis that the data vector was generated by tissue type "R"; $R = 1, 2, \ldots, K$. We then calculate the conditional probability density functions $p(x|H_R)$ (the probability density of data vector x, given that the pulse-echo record was generated by tissue type "R") using prior knowledge of the statistical properties of the pulse-echo records associated with each tissue type. The statistical properties associated with the tissue type are determined from statistical models based on sets of training data obtained from known tissue types. The values of the conditional probability for each possible tissue type represent likelihood functions which are logically compared and a predetermined decision rule is applied to select the tissue type which most probably generated the data vector.

The likelihood functions can be computed recursively from the data samples; that is the data samples can be processed one at a time, as they are received, and the likelihood functions updated with each new data sample. Recursive processing permits real time (on-line) tissue classification using dedicated microcomputer-based signal processors and allows continuous processing of new data until one tissue type hypothesis dominates under the decision rule.

Hypothesis testing techniques have been widely and effectively used in many signal processing applications of the prior art. A general discussion of these techniques and their application to specific prior art problems is set forth in the text *Uncertain Dynamic Systems* by Fred C. Schweppe, Prentice Hall, Inc., 1973 which is incorporated herein, by reference, as background material. The success of hypothesis testing methods is, however, critically dependent upon the validity of the statistical models of the underlying physical process which are incorporated in the hypothesis testing algorithm.

We have determined that hypothesis testing is a suitable method for tissue classification from ultrasound pulse echo data if a sequence of pulse-echo samples is modeled as an autoregressive process; that is if the samples satisfy the equation:

$$x_n = a_1 x_{n-1} + a_2 x_{n-2} + \ldots + a_L x_{n-L} + W_n$$

where $W_n$ is an uncorrelated random sequence (white noise) and the autoregressive parameters $[a_1, a_2, \ldots a_L]$ characterize the particular process. Estimates of these parameters can be obtained from "training sets" of pulse-echo data which are generated by known tissue types. Thus, each tissue type is characterized by a set of autoregressive parameters. Using the autoregressive parameters for each tissue type we construct an algorithm for recursively computing the likelihood function for any given pulse-echo data sequence.

The autoregressive parameters can be obtained from the training sets of data by either of two known methods. In the first method, the data are used to generate an estimate of the autocorrelation function using time averages. The estimate of the autocorrelation function is then used to generate the autoregressive parameters using the Durbin-Levinson algorithm (or some variation of the Durbin-Levinson algorithm).

In the second method, the autoregressive parameters are calculated directly from the data training sets using the Burg algorithm (or one of the many variations of the Burg algorithm).

Both of these methods, as well as their many variations, are described in *Non-Linear Methods of Spectral Analysis*, S. Haykin (Editor), Springer-Verlag, 1979, which is incorporated herein, by reference, as background material.

The sequence of tissue pulse-echo samples may, if desired, also be molded as an autoregressive moving average process.

Kalman filters can be utilized for the recursive computation of the likelihood functions. This technique is described in the text *Digital and Kalman Filtering* by S. M. Bozic, John Wiley and Sons, 1979 which is incorporated herein, by reference, as background material.

BRIEF DESCRIPTION OF THE DRAWINGS

The invention may be best understood by reference to the accompanying drawings in which:

FIGS. 4 through 6 are plots of the logarithms of likelihood functions which were recursively computed from echo samples generated in sponge samples; and FIGS. 7 through 9 are plots of the logarithms of likelihood functions which were recursively computed from ultrasound echo samples derived, in vivo, from human liver, pancreas and spleen tissue.

DESCRIPTION OF A PREFERRED EMBODIMENT

Figure 1:
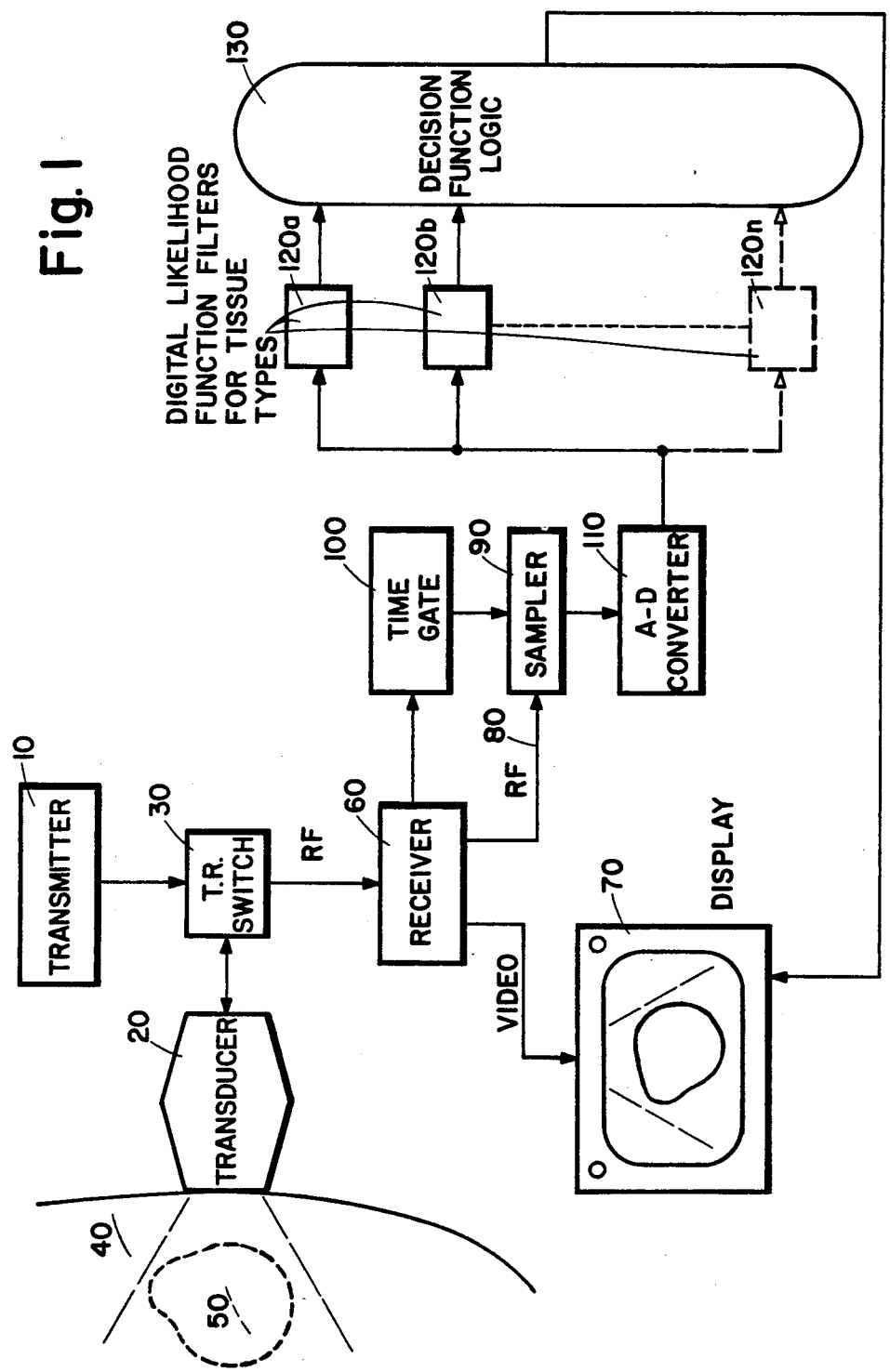
FIG. 1 schematically illustrates apparatus for classifying tissue in accordance with the invention.

FIG. 1 is a preferred embodiment of apparatus for tissue characterization in accordance with the invention. A transmitter 10 activates an ultrasound transducer 20 via a TR switch 30 to direct pulses of ultrasound energy into a test body 40 which may, for example, be a human abdomen. Ultrasound energy from the transmitter is scattered by body tissues including unknown tissues in a region 50. Portions of the scattered energy are returned as echoes to the transducers 20 and are directed via the TR switch into a receiver 60.

The receiver detects and processes the echo signals in a conventional manner to generate video signals which are utilized to generate an image on a display unit 70. The displayed image may, for example, be a conventional B-scan image of the internal structure of the body 40.

The amplified radio frequency echo signals from the receiver 60 are also transmitted via line 80 to a sampling circuit 90. A time gate 100 is operatively connected to the sampling circuit 90 in a manner which causes the sampler to extract a series of periodic samples of the values of received echo signals which were scattered from tissue in the unknown region 50. The operation of the time gate may, for example, be controlled in a known manner by means of a cursor which is manually set over a given region of the display 70 or may be triggered by high amplitude echoes which are scattered from the edges of the region 50. Signals representing the amplitude of the series of samples derived from the sampler 90 are digitized in an analog-to-digital converter 110. The series of digitized signals are then applied to a parallel chain of digital likelihood function filters 120a through 120n (more particularly described below). Each filter calculates the value of a likelihood function which represents the conditional probability that the series of sample signals were produced in a given tissue type. The output signals from the parallel filters are fed to decision function logic 130 which, using known algorithms, assigns one of the possible tissue types to the unknown tissue represented by the sample vector.

If the a priori probabilities of occurrence of the various tissue types are equal (or unknown) a preferred embodiment of the decision function logic assigns the unknown tissue as the tissue type associated with the likelihood function filter which produces the largest output signal. The decision function logic may, however, be modified in a known manner to choose the likelihood function having the largest aposteriori probability if the various tissue types have different a priori probabilities of occurrence or to minimize the expected penalty if there is a large penalty attached to misidentification errors of a specific type.

The output signal from the decision function logic 130 is routed to the display 70 where it is used to identify the tissue type of the unknown region; for example by display of a message associated with a cursor or by assigning a particular color or brightness level to pixels in an image of the region where the echo samples originated.

In an alternate embodiment of the invention the output signals of the likelihood function filters may be utilized (either directly or after processing in decision function logic) to modulate the color or intensity of the associated region in the display. In the latter case the saturation of color in the associated region could provide an indication of the confidence level of the tissue characterization for that region.

Figure 2:
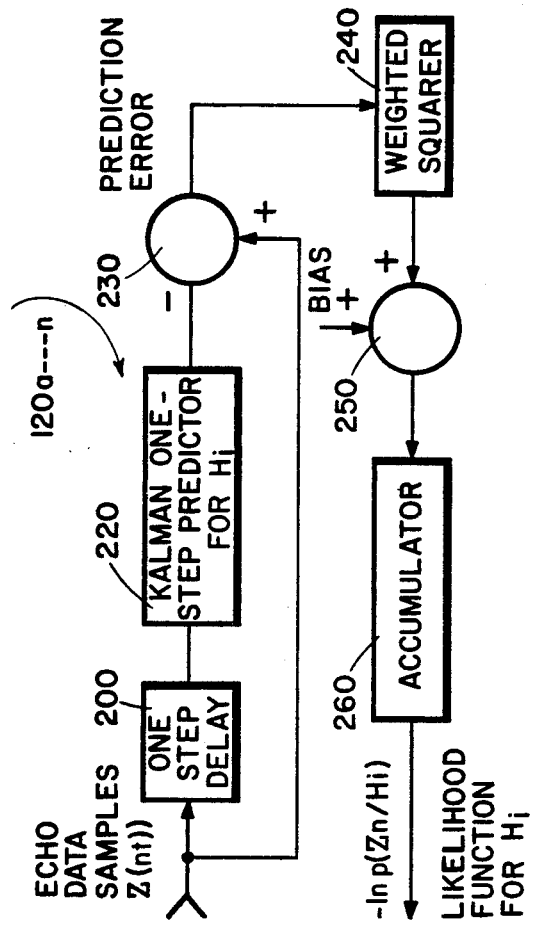
FIG. 2 illustrates a digital filter for extracting a likelihood function from a pulse-echo data vector.

FIG. 2 illustrates the typical filter for calculating the logarithm of the likelihood function for a given hypothesis $H_R$. The series of periodic data samples $Z(nT)$ is serially fed to the input of a delay stage 200 having a delay time T and to the positive input of a subtractor 230. The output of the delay stage 200 is fed through a one-step Kalman predictor error filter which characterizes the hypothesis $H_R$. The output of the Kalman filter 220 is fed to the negative input of the subtractor 230. The output of the subtractor thus represents the difference between the actual value and the predicted value for each component of the data vector: that is the prediction error of the Kalman filter. The prediction error is processed in a weighted squarer 240 and a bias signal is added to the output of the squarer in an adder stage 250. The signals from the output of the adder 250 are summed in an accumulator 260 whose output represents a likelihood function for the hypothesis which is modeled by the Kalman filter.

A Fortran computer program which represents the preferred embodiment for generating likelihood functions from data sample vectors is listed below. The scattering in the various tissue types are modeled as time invariant, autoregressive processes. The prediction error, which is called the innovations representations of the process, is assumed to be white and Gaussian. The program further functions to calculate the coefficients which characterize the autoregressive model for each tissue type from data vector samples which are obtained from echoes of known tissue regions.

Figure 3:
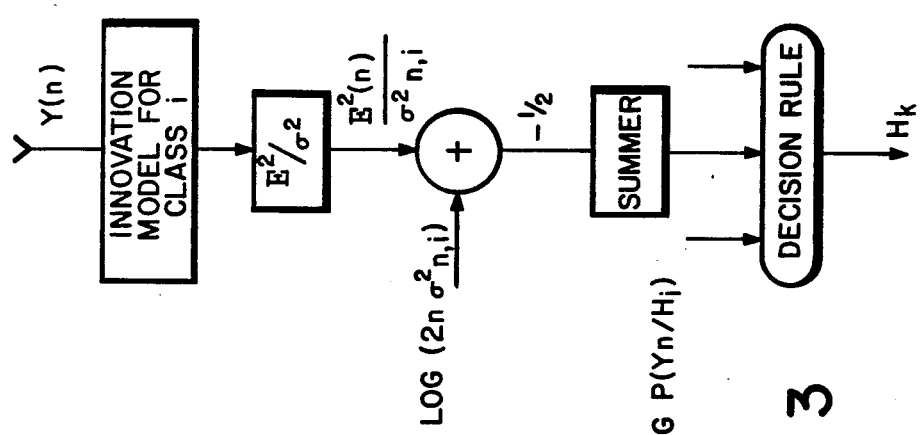
FIG. 3 is a flow chart for a preferred embodiment of a tissue classification algorithm.

In the program listing: the program TCP generates an autoregressive model for each of three classes of training sample data vectors (A-lines) and tests the models on other samples from tissue in the same classes;

the subroutine PRK obtains the lattice predictive model from data in program TCP;

the subroutine GETTCD reads data from a disc and normalizes it to zero mean and unit variance;

the subroutine PRERK, using the lattice model, obtains the Innovations process of the input data;

the subroutine APSPRB calculates a posteriori probabilities of one of three equally probably hypotheses using relative log likelihood functions;

FIG. 3 is a flow chart of the processor used to calculate to likelihood functions by the listed program.

EXAMPLE 1

Figure 5:
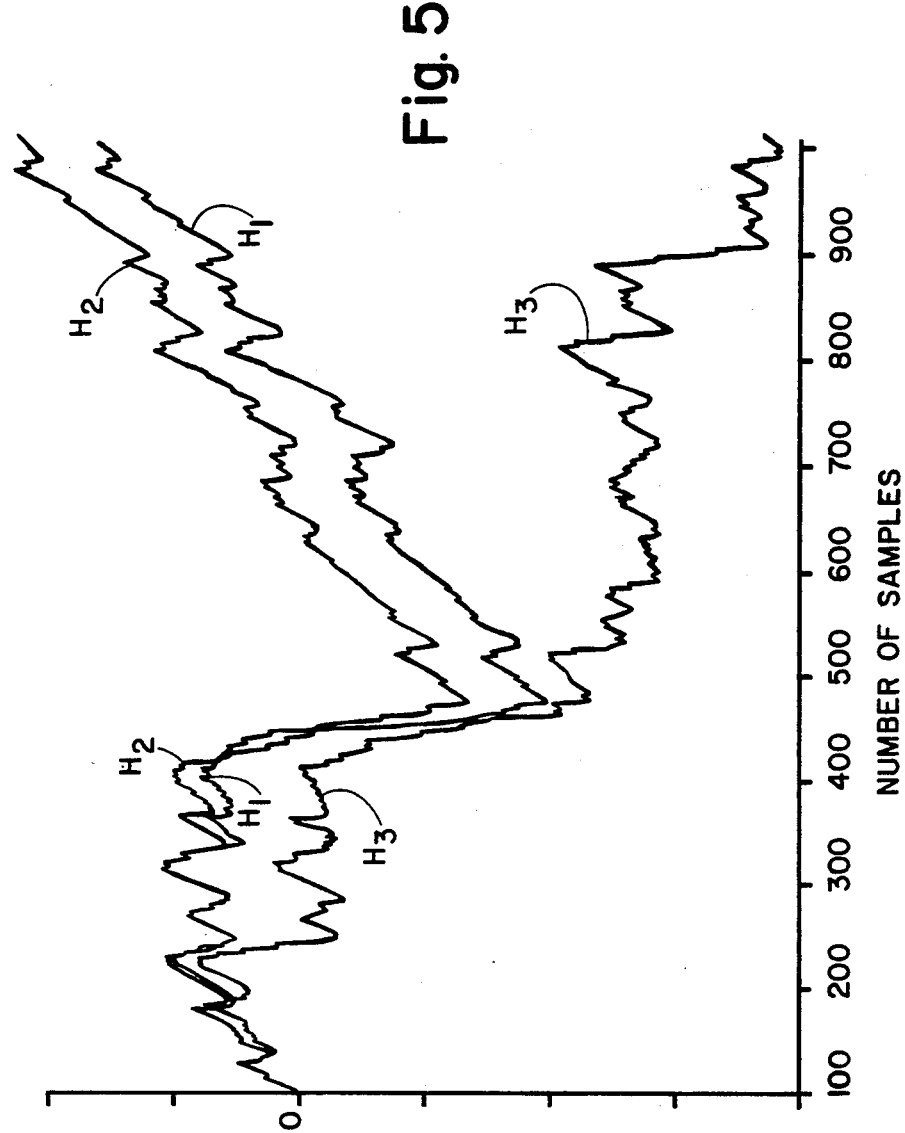
Figure 6:
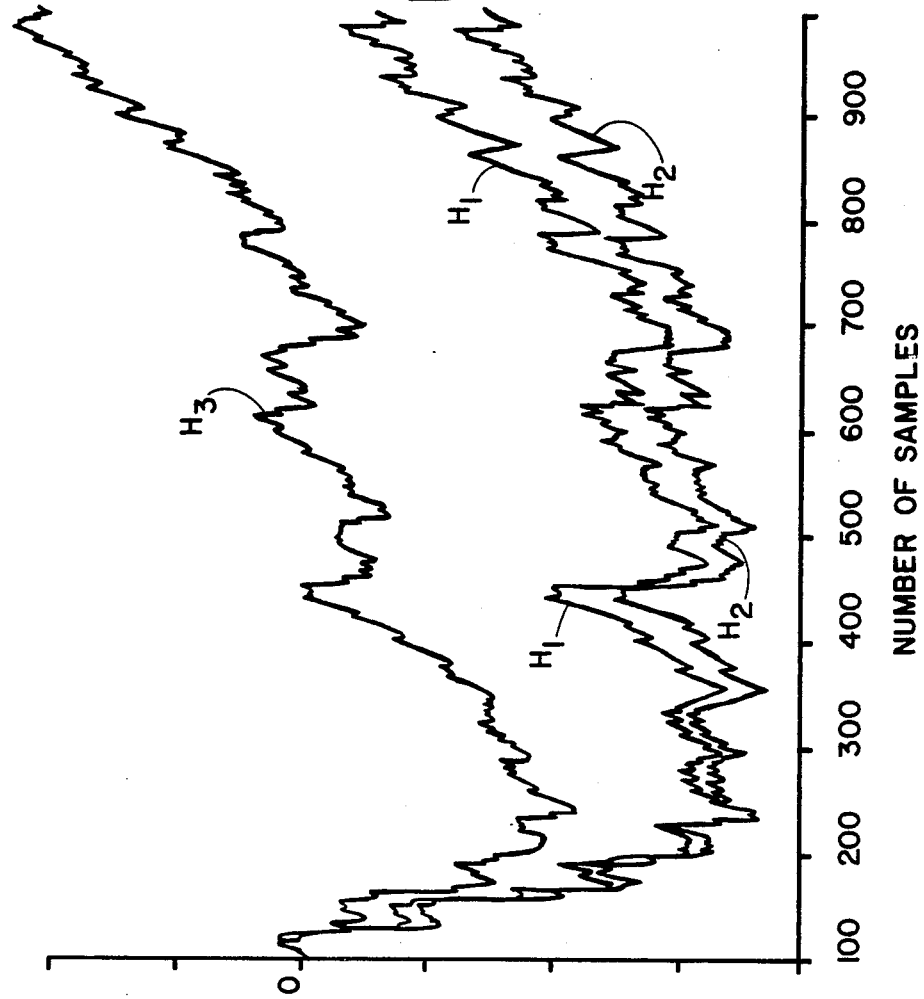

Pulse echo data was collected from samples of a natural sponge and from two different types of synthetic sponge using a 19 mm diameter, 3.5 MHz transducer in a water tank and a Philips 5580 B-scanner. The output of the scanner TGC amplifier was fed to a Biomation 8100 Transient Recorder (20 MHz sample rate, 5 bits/sample) which was interfaced to a DEC 11/60 minicomputer. The pulse-echo records from each sponge sample were divided into two sets; a training set and a test set. Parameters for the autoregressive model were generated, using the method set forth in the program listing, for each of the test samples. In this way autoregressive models were generated for each sponge type. Data vectors were then obtained from echoes which originated in the three test samples. FIG. 4 illustrates the values of the likelihood functions computed for a data vector derived from sponge sample 1 using the computed hypotheses based on models from the teaching samples of sponge types 1, 2, and 3. As illustrated, after a reasonable number of samples, the likelihood function associated with hypothesis 1 has the highest value thereby correctly identifying the sponge sample as type 1. FIGS. 5 and 6 illustrate similar computations for test samples of sponge types 2 and 3. In all cases the apparatus correctly identified the test sponge sample.

For comparison the power spectra of the pulse-echo records of the three sponge types were computed and were found to be essentially indistinguishable.

EXAMPLE 2

Figure 7:
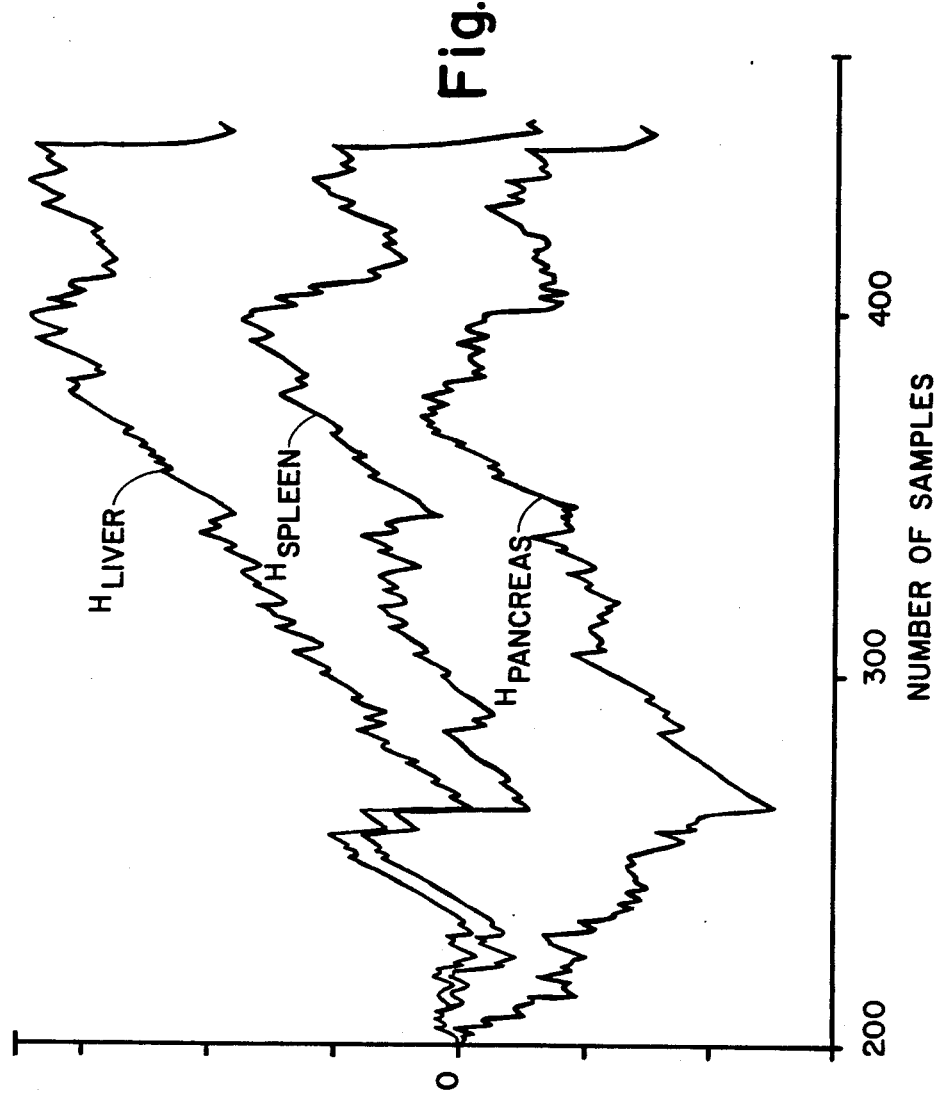
Figure 8:
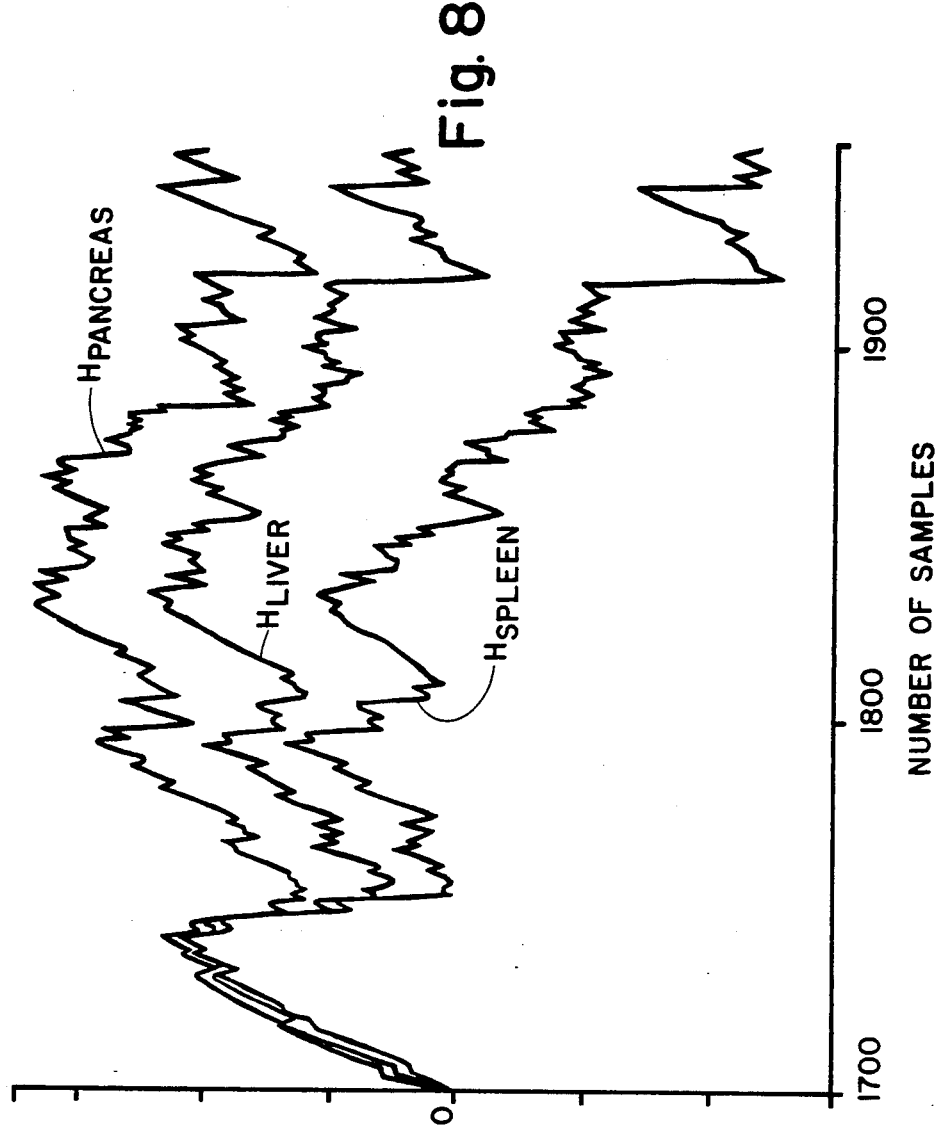

Training data and test data vectors were obtained from in vivo pulse-echo data from a human liver, spleen and pancreas and the procedures utilized with the sponge data were repeated. The computed likelihood functions are illustrated for liver test data vectors in FIG. 7, for pancreas test data vectors in FIG. 8 and for spleen test data vectors in FIG. 9. The filters correctly identified liver and pancreas pulse-echoes with a high degree of reliability. The algorithm correctly differentiated spleen data from liver but with substantially more difficulty and lower confidence than the other samples.

The preferred embodiment of the present invention characterizes tissue types on a basis of the statistical characteristics of samples of the amplitude of ultrasonic pulse-echoes. The statistical characteristics of other measured characteristics of pulse-echo data may however also be utilized in the computational algorithm. For example, the instantaneous frequency or phase of the reflected signal might be sampled in place of or in conjunction with the amplitude of the signal.

```
@PE TCP FORTRAN

C*****************************************************************
C    PROGRAM TCP
C
C    PROGRAM GENERATES AR MODEL FOR EACH THREE CLASSES OF TRAINING
C    SAMPLE A-LINES (REAL OR SYNTHETIC) AND TEST THE MODELS ON OTHER
C    SAMPLE A-LINES FROM THE SAME CLASSES
C
C
C*****************************************************************
C
      IMPLICIT REAL*8 (A-H, O-Z)
      REAL*8 DSIG(2048),RK(51,3),RKT(51),ERROR(51,3),ERRT(51),RINN(2048)
     &      ,RKS(51,3),AS(51,3)
      REAL XLL(2048,3)XPLT(1024),YPLT(1024),RES(2048)
      INTEGER IOR(3),IORS(3),ISTPT(3)
C
      DEFINE FILE 12(36,2048,U,IV4),13(36,2048,U,IV5),14(36,2048,U,IV6)
     &      ,15(36,2048,U,IV7),16(36,2048,U,IV8),17(36,2048,U,IV9)
C
C SPECIFICATIONS
C
50    WRITE(6,51)
51    FORMAT(/' TYPE:   FIRST RECORD AND # OF RECORDS FOR TRAINING'/
     &       '         THE SAME FOR THE RECORDS TO BE TESTED'/
     &       '         START PTS. FOR EACH CLASS'/
     &       '         # OF SAMPLES/RECORD'/
     &       '         MAX ORDER OF THE AR MODEL'/
     &  8X,'OPTION:  1=DISK DATA, 2=SYN DATA')
      READ(5,*) NFTR,NTR,NFTS,NTS,(ISTPT(I),I=1,3),NSAM,MOR,ISOPT
      IF(MINO(NFTR,NTR,NFTS,NTS).LT.1 .OR. MAXO(NFTR,NFTS).GT.12
     &   .OR. MAXO(NFTR+NTR,NFTS+NTS).GT.13 .OR. MOR.GT.50 .OR.
     &   ISOPT.LT.1 .OR. ISOPT.GT.2 .OR. NSAM.LT.2 .OR. NSAM.GT.2048)
     &   GOTO 50
      DO 59 I=1,3
         IF(ISTPT(I).LT.1 .OR. ISTPT(I)+NSAM.GT.2049) GOTO 50
59    CONTINUE
C
C    IF THE OPTION IS SYN. DATA
C
```

```
            IF(ISOPT .EQ. 1) GOTO 95
80      WRITE(6,81)
81      FORMAT(/' TYPE:'/
       & ' ORDER   OF AR MODEL (M) FOR CLASS 1 & K(I) I=1,M'/
       & ' THE SAME FOR CLASS 2 & 3, PLEASE ONE CLASS/LIN')
        DO 85 I=1,3
            READ(5,*) M,(RKS(J,I),J=1,M)
            IORS(I) = M
            IF(M.L).1 .OR. M.G(.50) GOTO 80
85      CONTINUE
C
C   CONVERT A-COEFS. TO K-COEFS. BY SUB. KTOA
C
        DO 88 I=1,3
            CALL KTOA(RKS(1,I),AS(1,I),IORS(I))
88      CONTINUE
C
C   OBTAIN K-COEFS. FROM TRAINING DATA
C
95      DO 109 ISP=1,3
            CALL PRK(ISP,NFTR,NTR,ISTPT(ISP),NSAM,MOR,RK(1,ISP),
       &            ERROR(1,ISP),1,ISOPT,AS(1,ISP),IORS(ISP),DSIG)

CALL PRK(ISP,NFTS,NTS,ISTPT(ISP),NSAM,MOR,RKT,ERRT,2,
       &            ISOPT,AS(1,ISP),IORS(ISP),DSIG)
109     CONTINUE
C
C   HYPOTHESIS TESTING
C
150     WRITE(6,151)
151     FORMAT(/' TYPE:   THE ORDER OF THE AR MODEL FOR CLASS 1 A-LINES'/
       &      '          THE SAME FOR CLASS 2'/8X,'THE SAME FOR CLASS 3'/
       &      8X,'THE REDUCTION FACTOR & MAX # OF POINTS FOR PLOTS'/
       &      8X,'1 = EQUAL VARIANCES    2 = NOT 1')
        READ(5,*) (IOR(I),I=1,3),IRDC,MNPT,IEQVAR
        DO 153 I=1,3
            IF(IOR(I).LT.0 .OR. IOR(I).GT.50) GOTO 150
153     CONTINUE
        IORMAX = MAXO(IOR(1),IOR(2),IOR(3))
        IF(IRDC.LT.1 .OR. MNPT.LT.2) GOTO 150
        NPT = NSAM/IRDC
        IF(NPT.GT.MNPT) NPT = MNPT
C
        DO 299 I=1,12
C
            IR = I
            DO 259 ISP=1,3
                IF(ISOPT.EQ.1) CALL GETTCD(DSIG,1,2048,IR,ISP)
                ISEED = IR*3 + ISP - 1
                IF(ISOPT.EQ.2) CALL GETDR(AS(1,ISP),IORS(ISP),1.,DSIG,2048,
       &                                  ISEED)
C
                IF(I.GT.1) GOTO 175
                DO 170 J=1,NSAM
                    YPLT(J) = DSIG(J)
                    XPLT(J) = J
170             CONTINUE
C               WRITE(6,172) ISP
172             FORMAT(//T30,'NORMALIZED A-LINE FROM CLASS',I4)
C               CALL PLOT(XPLT,YPLT,300)
175             DO 229 IH=1,3
C
C   GENERATE THE INNOVATIONS PROCESS BY SUB. PRERK
C
                    CALL PRERK(DSIG,2048,RK(1,IH),IOR(IH),RINN)
C
C   CALCULATE THE LOG-LIKELIHOOD FUNCTIONS SEQUENTIALY
C
```

```
                        VAR = ERROR(IOR(IH),IH)
                        IF(IEQVAR.EQ.1) VAR = 1.
                        BIAS = -.5*DLOG(VAR)
                        XT = 0.
                        DO 211 J=1,2048
                           IND = J
                           IF(IND .LE. IORMAX) GOTO 209
                              XT = XT - .5*RINN(IND)**2/VAR
209                        CONTINUE
                           XLL(J,IH) = XT + J*BIAS
                           RES(J) = RINN(IND)
211                     CONTINUE
                        IWR = (ISP - 1)*12 + I
                        IFILE = 11 + IH
                        WRITE(IFILE'IWR) RES
                        IWR = (I-1)*3 + IH
                        IFILE = 14 + ISP
                        WRITE(IFILE'IWR) (XLL(J,IH),J=1,2048)
229               CONTINUE
C
C
259         CONTINUE
299      CONTINUE
         STOP
         END
C
C*****************************************************************************
C
      SUBROUTINE PRK(ISP,NF,N,IST,NS,MOR,RK,ERROR,IC1,IC2,AS,IORS,DSIG)
C
C  SUBROUTINE OBTAINS THE LATTICE PREDICTIVE MODEL FROM DATA
C
      IMPLICIT REAL*8 (A-H,O-Z)
      REAL*8 PHI(51,51),PHIO(51,51),RK(51),TK(51,12),SCR(51),DSIG(2048)
     &      ,A(51),ERROR(51),AS(IORS)
      REAL SPECT(129),SPAXIS(129)
C
      DO 3 J=1,129
         SPECT(I) = 0.
3     CONTINUE
      DO 9 J=1,51
         DO 9 K=1,51
9     CONTINUE
C
      DO 39 I=1,N
         IR = NF + I - 1
         IF(IC2.EQ.1) CALL GETTCD(DSIG,IST,NS,IR,ISP)
         ISEED = IR*3 + ISP - 1
         IF(IC2.EQ.2) CALL GETDR(AS,IORS,1.,DSIG,NS,ISEED)
C
         CALL PRDTMP(SPECT,DSIG,NS)
C
C  COMPUTE THE COVARIANCE MATRIX
C
         CALL DCOVR1(DSIG,NS,MOR,PHI,51)
         MORP1 = MOR + 1
C
         DO 19 J=1,MORP1
            DO 19 K=1,MORP1
            PHIO(K,J) = PHIO(K,J) + PHI(K,J)
C
19       CONTINUE
C
         DO 29 M=1,MOR
            CALL DCLHRM(PHI,51,M,A,TK(M,I),TERR,SCR)
29       CONTINUE
39    CONTINUE
C
```

```
          DO 42 J=1,129
              SPECT(J) = SPECT(J)/FLOAT(N)
              SPAXIS(J) = FLOAT(J-1)/128.
42        CONTINUE
C
          DO 49 M=1,MOR
              CALL DCLHRM(PHIO,51,M,A,RK(M),ERROR(M),SCR)
              ERROR(M) = ERROR(M)/((NS - M)*N*2)
49        CONTINUE
C
C   PRINT THE K CHART
C
          DO 129 M=1,MOR
              AVK = 0.D0
              DO 89 I=1,N
                  AVK = AVK + TK(M,I)
89            CONTINUE
              AVK = AVK/N
              WRITE(6,91) M,(TK(M,I),I=1,N),AVK,RK(M),ERROR(M)
91            FORMAT(I3,15F8.6)
129       CONTINUE
C          CALL PLOT(SPAXIS,SPECT,129)
          RETURN
          END
C
          SUBROUTINE GETTCD(DSIG,IST,NS,IR,ISP)
C
C   SUBROUTINE READS THE DATA FROM DISC, THE NORMALIZE THEM TO
C   ZERO-MEAN AND UNIT-VARIANCE.
C
          REAL*8 DSIG(NS),SQ,SM,DTMP
          INTEGER*2 ID(2048)
C
          DEFINE FILE9(12,4096,L,IV1),10(12,4096,L,IV2),11(12,4096,L,IV3)
C
          J = ISP + 8
          READ(J'IR) ID
          SM = 0.D0
          SQ = 0.D0
          MSZ = 55
          MSZ2 = MSZ/2
          DO 19 J=1,NS
              I = J + IST - 1
              IF(J.NE.1) GOTO 15
              DO 11 L2=1,MSZ2
                  L = L2 + IST - 1
                  SM = SM + ID(L)
                  SQ = SQ + ID(L)*ID(L)
11            CONTINUE
15            IADD = I + MSZ2
              ISBT = I - MSZ2 - 1
              IF(IADD.GT.NS+IST-1) GOTO 16
              SM = SM + ID(IADD)
              SQ = SQ + ID(IADD)*ID(IADD)
16            IF(ISBT .LT. IST) GOTO 17
              SM = SM - ID(ISBT)
              SQ = SQ - ID(ISBT)*ID(ISBT)
17            FMZ = MSZ
              IF(J.LE.MSZ2) FMZ = MSZ2 + J
              IF(NS-J .LT. MSZ2) FMZ = MSZ + NS - J + 1
              DSIG(J) = ID(I) - SM/FMZ
              DTMP = DSQRT(SQ/FMZ - (SM/FMZ)**2)
              IF(DTMP .NE. 0.D0) DSIG(J) = DSIG(J)/DTMP
19        CONTINUE
          RETURN
          END
C
C***********************************************************************
C
```

```
      SUBROUTINE PRERK(X,NS,RK,IOR,Y)
C
C  SUBROUTINE OBTAINS (Y) THE INNOVATION PROCESS OF (X) USING
C  THE LATTICE MODEL WITH COEFFS. (RK)
C
      IMPLICIT REAL*8 (A-H,O-Z)
      DO 9 I=1,IOR
         Z(I) = 0.D0
9     CONTINUE
C
      DO 99 I=1,NS
         E = X(I)
         W(1) = E
         DO 39 J=2,IOR
            JM1 = J - 1
            W(J) = Z(JM1) + RK(JM1)*E
            E = E + RK(JM1)*Z(JM1)
39       CONTINUE
         Y(I) = E + RK(IOR)*Z(IOR)
         DO 49 J=1,IOR
            Z(J) = W(J)
49       CONTINUE
99    CONTINUE
      RETURN
      END
C
C***********************************************************************
C
      SUBROUTINE KTOA(RK,A,IOR)
C
      REAL*8 A(IOR),RK(IOR),B(51)
C
      A(1) = RK(1)
      IF(IOR .LE. 1) RETURN
C
      DO 19 M=2,IOR
         A(M) = RK(M)
         MM1 = M - 1
         DO 12 I=1,MM1
            B(I) = A(I) + RK(M)*A(M-I)
12       CONTINUE
         DO 15 I=1,MM1
            A(I) = B(I)
15       CONTINUE
19    CONTINUE
      RETURN
      END
C***********************************************************************

C***********************************************************************
      SUBROUTINE APSPRB(P,T1,T2)
C
C  SUBROUTINE CALCULATES APOSTERIORI PROBABILITIES (P) OF ONE OF
C  THE THREE EQUALY PROBABLE HYPOTHESES USING REALTIVE
C  LOG-LIKELIHOOD FUNCTIONS (T1,T2)
C
      REAL*8 T1,T2
C
      P = 0.
      IF(T1.GT.50. .OR. T2.GT.50.) RETURN
      P = 1.
      IF(T1.GT.-50.) P = P + DEXP(T1)
      IF(T2.GT.-50.) P = P + DEXP(T2)
      P = 1./P
      RETURN
      END
C
C***********************************************************************
```

What is claimed:

1. A method for remote identification of a tissue using ultrasound, comprising the steps of:
   directing ultrasound energy into an unknown tissue;
   measuring values of a characteristic of echoes of the ultrasound which are scattered from the unknown tissue;
   accumulating a statistically significant sample of the measured values of the characteristic;
   filtering the accumulated sample to determine, for each of a plurality of predetermined mathematical models, each of which is associated with a possible tissue type, a signal which is a measure of the likelihood that the accumulated sample of measured values was generated by said mathematical model;
   applying the the filtered signals as inputs of a predetermined logical decision function which selects one of the models which most likely produced the sample; and
   assigning the tissue type which is associated with the chosen model as the identity of the unknown tissue.

2. The method of claim 1 wherein the step of directing energy comprises directing pulses of ultrasound energy into the tissue.

3. The method of claim 1 wherein the step of directing energy comprises directing pulses of ultrasound energy into the tissue and wherein the measured values are values of the instantaneous amplitude of the echoes.

4. The method of claim 3 wherein the step of filtering comprises calculating the logarithm of the likelihood function for each possible tissue type.

5. The method of claim 4 wherein the step of combining the filtered signals comprises choosing the mathematical model having the largest likelihood function.

6. The method of claim 4 wherein the step of combining the filtered signals comprises choosing the model having the largest a posteriori probability.

7. The method of claim 6 further comprising the step of generating an image from the values of the scattered echoes and wherein the step of assigning the tissue type comprises identifying pixels of the image with specific brightness or color values which are associated with the associated tissue type.

8. The method of claim 6, wherein the step of filtering comprises filtering the accumulated sample in one or more filters which are characterized by numerical parameters and further comprising the step of determining numerical parameters which characterize each possible tissue type from samples of echoes which are scattered from a known sample of the particular tissue type.

9. The method of claim 4 wherein there is a known penalty attached to misidentification of one or more tissue types and wherein the step of combining the filtered signals comprises choosing the mathematical model which minimizes the expected value of the penalty.

10. The method of claim 9 further comprising the step of generating an image from the values of the scattered echoes and wherein the step of assigning the tissue type comprises identifying pixels of the image with specific brightness or color values which are associated with the associated tissue type.

11. The method of claim 9, wherein the step of filtering comprises filtering the accumulated sample in one or more filters which are characterized by numerical parameters and further comprising the step of determining numerical parameters which characterize each possible tissue type from samples of echoes which are scattered from a known sample of the particular tissue type.

12. The method of claim 3 where the step of filtering determines a signal which is a measure of the likelihood that the accumulated sample of the echo amplitudes was generated by autoregressive mathematical models.

13. The method of claim 12 wherein the step of filtering comprises filtering the accumulated sample with Kalman one-step prediction error filters.

14. The method of claim 13 further comprising the step of generating an image from the values of the scattered echoes and wherein the step of assigning the tissue type comprises identifying pixels of the image with specific brightness or color values which are associated with the associated tissue type.

15. The method of claim 13, wherein the step of filtering comprises filtering the accumulated sample in one or more filters which are characterized by numerical parameters and further comprising the step of determining numerical parameters which characterize each possible tissue type from samples of echoes which are scattered from a known sample of the particular tissue type.

16. The method of claim 12 wherein the step of combining the filtered signals comprises choosing the mathematical model having the largest likelihood function.

17. The method of claim 16, wherein the step of filtering comprises filtering the accumulated sample in one or more filters which are characterized by numerical parameters and further comprising the step of determining numerical parameters which characterize each possible tissue type from samples of echoes which are scattered from a known sample of the particular tissue type.

18. The method of claim 12 wherein the step of combining the filtered signals comprises choosing the model having the largest a posteriori probability.

19. The method of claim 12 wherein there is a known penalty attached to misidentification of one or more tissue types and wherein the step of combining the filtered signals comprises choosing the mathematical model which minimizes the expected value of the penalty.

20. The method of claim 12 further comprising the step of generating an image from the values of the scattered echoes and wherein the step of assigning the tissue type comprises identifying pixels of the image with specific brightness or color values which are associated with the associated tissue type.

21. The method of claim 12, wherein the step of filtering comprises filtering the accumulated sample in one or more filters which are characterized by numerical parameters and further comprising the step of determining numerical parameters which characterize each possible tissue type from samples of echoes which are scattered from a known sample of the particular tissue type.

22. The method of claim 3 wherein the step of filtering determines a signal which is a measure of the likelihood that the accumulated sample of echo amplitudes was generated by autoregressive moving average mathematical models.

23. The method of claim 3 wherein the step of filtering comprises recursively filtering valves of the data sample as successive amplitude values are accumulated.

24. The method of claim 23 wherein the step of combining the filtered signals comprises choosing the mathematical model having the largest likelihood function.

25. The method of claim 23 wherein the step of combining the filtered signal comprises choosing the model having the largest a posteriori probability.

26. The method of claim 23 wherein there is a known penalty attached to misidentification of one or more tissue types and wherein the step of combining the filtered signals comprises choosing the mathematical model which minimizes the expected value of the penalty.

27. The method of claim 23, wherein the step of filtering comprises filtering the accumulated sample in one or more filters which are characterized by numerical parameters and further comprising the step of determining numerical parameters which characterize each possible tissue type from samples of echoes which are scattered from a known sample of the particular tissue type.

28. The method of claim 3 wherein the step of combining the filtered signals comprises choosing the mathematical model having the largest likelihood function.

29. The method of claim 28 further comprising the step of generating an image from the values of the scattered echoes and wherein the step of assigning the tissue type comprises identifying pixels of the image with specific brightness or color values which are associated with the associated tissue type.

30. The method of claim 28, wherein the step of filtering comprises filtering the accumulated sample in one or more filters which are characterized by numerical parameters and further comprising the step of determining numerical parameters which characterize each possible tissue type from samples of echoes which are scattered from a known sample of the particular tissue type.

31. The method of claim 3 further comprising the step of generating an image from the values of the scattered echoes and wherein the step of assigning the tissue type comprises identifying pixels of the image with specific brightness or color values which are associated with the associated tissue type.

32. The method of claim 3, wherein the step of filtering comprises filtering the accumulated sample in one or more filters which are characterized by numerical parameters and further comprising the step of determining numerical parameters which characterize each possible tissue type from samples of echoes which are scattered from a known sample of the particular tissue type.

33. The method of claim 1, wherein the step of filtering comprises filtering the accumulated sample in one or more filters which are characterized by numerical parameters and further comprising the step of determining numerical parameters which characterize each possible tissue type from samples of echoes which are scattered from a known sample of the particular tissue type.

34. A method for manufacturing a filter which extracts, from a statistically significant sample of the values of signals which represent detected echoes of ultrasound which are scattered from unknown tissue, a signal which is a measure of the likelihood that the accumulated sample was generated by a mathematical model which characterizes a known tissue type, comprising the steps of:

directing ultrasound energy into a sample of the known tissue;

detecting values characteristic of echoes of the ultrasound which are scattered from the known tissue;

accumulating a statistically significant sample of the detected characteristic values;

calculating, from the accumulated sample, autoregressive parameters which characterize an autoregressive process which models the sample values; and constructing a Kalman predictive filter which incorporates the determined autoregressive parameters.

35. The method of claim 34 wherein the step of detecting values of a characteristic of the echoes comprises detecting samples of the instantaneous amplitude of the echoes.

36. The method of claim 35 wherein the known tissue type comprises a tissue selected from the class of tissues consisting of human liver tissue, human pancreas tissue, and human spleen tissue.

37. A filter manufactured by the process of claim 36.

38. A filter manufactured by the process of claim 35.

39. A filter manufactured by the process of claim 34.

40. Apparatus for remote identification of a tissue comprising:

means for directing ultrasound energy into an unknown tissue;

means for detecting a characteristic of echoes of the ultrasound which are scattered from the unknown tissue;

means for accumulating a statistically significant sample of signals which represent values of the detected characteristic;

a plurality of filter means, each of which function to filter the accumulated sample to extract a signal which is a measure of the likelihood that the accumulated sample was generated by an associated, predetermined mathematical model, wherein each of said mathematical models is associated with a possible tissue type; and means which apply the signals extracted by the filters, as inputs to a predetermined logical decision function to select the extracted signal which is associated with the model which most likely produced the sample and assign the tissue type associated with the model producing the chosen signal as the identity of the unknown tissue.

41. The apparatus of claim 40 wherein for directing energy direct pulses of ultrasound energy into the unknown tissue and wherein the means which detect the characteristic of the echoes extracts a time sequence of samples of the value of the instantaneous amplitude of the echoes.

42. The apparatus of claim 41 wherein the mathematical models associated with the filter means are autoregressive models.

43. The apparatus of claim 42 wherein the filter means comprise Kalman one step error prediction filters.

44. The apparatus of claim 43 wherein the means for combining signals choose the extracted signal having the largest value.

45. The apparatus of claim 43, further comprising means for displaying an image of at least the unknown tissue and wherein the means for combining the filtered signals functions to identify the unknown tissue by assigning a predetermined brightness and/or color value with associated pixels of the displayed image.

46. The apparatus of claim 43 wherein the filter means comprise one or more filters which are characterized by a series of autoregressive parameters which are produced by the process of:

directing pulses of ultrasound energy into a sample of a known tissue type;

detecting a sequence of values of the instantaneous amplitude of echoes of the ultrasound which are scattered from the known tissue type;

accumulating a statistically significant sample of the detected amplitudes; and calculating values of autoregressive parameters which model the sequence of accumulated samples as an autoregressive process and incorporating the calculated values in the filter.

47. The apparatus of claim 42 wherein the filter means operate recursively to process data samples as they are accumulated.

48. The apparatus of claim 47 wherein the filter means comprise one or more filters which are characterized by a series of autoregressive parameters which are produced by the process of:

directing pulses of ultrasound energy into a sample of a known tissue type;

detecting a sequence of values of the instantaneous amplitude of echoes of the ultrasound which are scattered from the known tissue type;

accumulating a statistically significant sample of the detected amplitudes; and calculating values of autoregressive parameters which model the sequence of accumulated samples as an autoregressive process and incorporating the calculated values in the filter.

49. The apparatus of claim 42 wherein the means for combining signals choose the extracted signal having the largest value.

50. The apparatus of claim 42 wherein the means for combining signals choose the extracted signal having the largest value.

51. The apparatus of claim 42, further comprising means for displaying an image of at least the unknown tissue and wherein the means for combining the filtered signals functions to identify the unknown tissue by assigning a pedetermined brightness and/or color value with associated pixels of the displayed image.

52. The apparatus of claim 42 wherein the filter means comprise one or more filters which are characterized by a series of autoregressive parameters which are produced by the process of:

directing pulses of ultrasound energy into a sample of a known tissue type;

detecting a sequence of values of the instantaneous amplitude of echoes of the ultrasound which are scattered from the known tissue type;

accumulating a statistically significant sample of the detected amplitudes; and calculating values of autoregressive parameters which model the sequence of accumulated samples as an autoregressive process and incorporating the calculated values in the filter.

53. The apparatus of claim 41 wherein the mathematical models associated with the filters are autoregressive moving average models.

54. The apparatus of claim 41 wherein the means for combining signals choose the extracted signal having the largest value.

55. The apparatus of claim 54 wherein the filter means comprise one or more filters which are characterized by a series of autoregressive parameters which are produced by the process of:

directing pulses of ultrasound energy into a sample of a known tissue type;

detecting a sequence of values of the instantaneous amplitude of echoes of the ultrasound which are scattered from the known tissue type;

accumulating a statistically significant sample of the detected amplitudes; and calculating values of autoregressive parameters which model the sequence of accumulated samples as an autoregressive process and incorporating the calculated values in the filter.

56. The apparatus of claim 41, further comprising means for displaying an image of at least the unknown tissue and wherein the means for combining the filtered signals functions to identify the unknown tissue by assigning a predetermined brightness and/or color value with associated pixels of the displayed image.

57. The apparatus of claim 41 wherein the filter means comprise one or more filters which are characterized by a series of autoregressive parameters which are produced by the process of:

directing pulses of ultrasound energy into a sample of a known tissue type;

detecting a sequence of values of the instantaneous amplitude of echoes of the ultrasound which are scattered from the known tissue type;

accumulating a statistically significant sample of the detected amplitudes; and calculating values of autoregressive parameters which model the sequence of accumulated samples as an autoregressive process and incorporating the calculated values in the filter.

58. The apparatus of claim 40 wherein the means for combining signals choose the extracted signal having the largest value.

59. The apparatus of claim 40, further comprising means for displaying an image of at least the unknown tissue and wherein the means for combining the filtered signals functions to identify the unknown tissue by assigning a predetermined brightness and/or color value with associated pixels of the displayed image.

60. The apparatus of claim 40 wherein the filter means comprise one or more filters which are characterized by a series of autoregressive parameters which are produced by the process of:

directing pulses of ultrasound energy into a sample of a known tissue type;

detecting a sequence of values of the instantaneous amplitude of echoes of the ultrasound which are scattered from the known tissue type;

accumulating a statistically significant sample of the detected amplitudes; and calculating values of autoregressive parameters which model the sequence of accumulated samples as an autoregressive process and incorporating the calculated values in the filter.

* * * * *